US007217360B2

(12) United States Patent
Brann

(10) Patent No.: US 7,217,360 B2
(45) Date of Patent: May 15, 2007

(54) MULTI COLUMN CHROMATOGRAPHY SYSTEM

(75) Inventor: John Brann, Shrewsbury, MA (US)

(73) Assignee: Cohesive Technologies Inc., Franklin, MA (US)

( * ) Notice: Subject to any disclaimer, the term of this patent is extended or adjusted under 35 U.S.C. 154(b) by 0 days.

(21) Appl. No.: 11/387,354

(22) Filed: Mar. 23, 2006

(65) Prior Publication Data
US 2006/0163133 A1    Jul. 27, 2006

Related U.S. Application Data

(62) Division of application No. 10/970,833, filed on Oct. 21, 2004, now Pat. No. 7,018,540, which is a division of application No. 10/671,900, filed on Sep. 26, 2003, now Pat. No. 6,808,635, which is a division of application No. 09/750,438, filed on Dec. 28, 2000, now Pat. No. 6,635,173.

(51) Int. Cl.
 B01D 15/02    (2006.01)
(52) U.S. Cl. ............... 210/198.2; 210/656; 210/659; 210/143
(58) Field of Classification Search ............... 210/635, 210/656, 659, 101, 143, 198.2; 422/70; 436/161
See application file for complete search history.

(56) References Cited

U.S. PATENT DOCUMENTS

| 4,003,243 | A | 1/1977 | Blu .................. 210/198.2 |
| 4,036,704 | A | 7/1977 | Takata ............... 210/198.2 |
| 4,775,481 | A | 10/1988 | Allington ............ 210/198.2 |
| 4,781,824 | A | 11/1988 | Allington ............ 210/101 |
| 4,797,207 | A | 1/1989 | Honganen et al. ...... 210/198.2 |
| 4,806,250 | A | 2/1989 | Takata ............... 210/198.2 |
| 4,919,595 | A | 4/1990 | Likuski et al. ....... 417/18 |
| 4,981,597 | A | 1/1991 | Allington et al. ..... 210/656 |

(Continued)

FOREIGN PATENT DOCUMENTS

JP    S59-114238    7/1984

(Continued)

OTHER PUBLICATIONS

Zeng, "Developments of a Fully Automated Parallel HPLC/Mass Spectrometry System", Anal. Chem. 1998, 70, pp. 4380-4388.

(Continued)

*Primary Examiner*—Ernest G. Therkorn
(74) *Attorney, Agent, or Firm*—Grossman, Tucker, Perreault + Pfleger, PLLC

(57) ABSTRACT

The present invention relates to a method and apparatus for chromatographically analyzing each of a plurality of samples in detector, comprising an autosampler to contain a plurality of samples for chromatographic analysis and a plurality of chromatographic systems, each system comprising one or more pumps and one or more chromatography columns. A detector is included for detecting compounds in the samples from each of the chromatography systems along with a valve positioned between the detector and the plurality of chromatography systems, the valve permitting each sample to reach the detector in sequence. A computer control device is included which adjusts the introduction of samples from the autosampler into the plurality of chromatography systems as well as the position of the valve to sequentially separate and deliver compounds within the samples to the detector.

5 Claims, 8 Drawing Sheets

U.S. PATENT DOCUMENTS

| | | | |
|---|---|---|---|
| 5,039,409 A | 8/1991 | Blaffert et al. | 210/198.2 |
| 5,040,126 A | 8/1991 | Allington | 702/47 |
| 5,045,196 A | 9/1991 | Fang | 210/278 |
| 5,071,624 A | 12/1991 | Sperling | 210/198.2 |
| 5,242,586 A | 9/1993 | Ransohoff | 210/198.2 |
| 5,457,626 A | 10/1995 | Wolze | 210/198.2 |
| 5,543,315 A | 8/1996 | Sugiyama | 210/198.2 |
| 5,772,874 A | 6/1998 | Quinn et al. | 210/198.2 |
| 5,795,469 A | 8/1998 | Quinn et al. | 210/198.2 |
| 5,919,368 A | 7/1999 | Quinn et al. | 210/635 |
| 5,947,689 A | 9/1999 | Schick | 417/19 |
| 5,968,367 A | 10/1999 | Quinn et al. | 210/656 |
| 6,019,897 A | 2/2000 | Horsman | 210/198.2 |
| 6,054,047 A | 4/2000 | Hindsgaul | 210/198.2 |
| 6,066,848 A | 5/2000 | Kassel et al. | 250/288 |
| 6,080,318 A | 6/2000 | Gumm | 210/198.2 |
| 6,110,362 A | 8/2000 | Quinn et al. | 210/198.2 |
| 6,149,816 A | 11/2000 | Quinn et al. | 210/635 |
| 6,197,198 B1 | 3/2001 | Messinger et al. | 210/656 |
| 6,210,571 B1 | 4/2001 | Zambias | 210/198.2 |
| 6,296,771 B1 | 10/2001 | Miroslav | 210/656 |
| 6,309,541 B1 | 10/2001 | Maiefski | 210/198.2 |
| 6,318,157 B1 | 11/2001 | Corso | 210/198.2 |
| 6,344,172 B1 | 2/2002 | Afeyan et al. | 422/70 |
| 6,355,163 B2 | 3/2002 | Hindsgaul | 210/198.2 |
| 6,365,105 B1 | 4/2002 | Waters et al. | 422/70 |
| 6,458,273 B1 | 10/2002 | Krakover | 210/198.2 |
| 6,491,816 B2 | 12/2002 | Petro | 210/198.2 |
| 6,712,085 B2 | 3/2004 | Weissgerber et al. | 137/12 |
| 6,911,151 B1 | 6/2005 | Muller-Kuhrt et al. | 210/656 |

FOREIGN PATENT DOCUMENTS

| | | |
|---|---|---|
| JP | S60-011690 | 1/1985 |
| JP | H01-131457 | 5/1989 |
| JP | H04-110656 | 4/1992 |
| JP | H05-302915 | 11/1993 |
| JP | H08-159930 | 6/1996 |
| JP | H09-015221 | 1/1997 |
| JP | H11-133011 | 5/1999 |
| JP | H11-326300 | 11/1999 |
| JP | 2000-266738 | 9/2000 |

OTHER PUBLICATIONS

Japanese Office Action including English language translation of the JP Office Action dated Sep. 13, 2006 issued in a counterpart Japanese Patent Application No. 2002-554200 filed Jun. 27, 2003.
Japanese Office Action including English language translation of the JP Office Action dated Sep. 25, 2006 issued in a counterpart Japanese Patent Application No. 2006-113556 filed Apr. 17, 2006 (which is a Divisional of counterpart Japanese Patent Application No. 2002-554200 filed Jun. 27, 2003).

Staggered starts synchronized with the detector

```
┌─────────────────────────────────────────────────────────────┐
│  Check that an autosampler/probe is ready to start a sample and that │
│       sufficient time has passed since the last sample start.        │
└─────────────────────────────────────────────────────────────┘
                              ↓
┌─────────────────────────────────────────────────────────────┐
│    Check that a chromatographic system is ready to accept a sample.  │
└─────────────────────────────────────────────────────────────┘
                              ↓
┌─────────────────────────────────────────────────────────────┐
│   Determine which sample corresponds with the ready chromatographic  │
│                              system.                                  │
└─────────────────────────────────────────────────────────────┘
                              ↓
┌─────────────────────────────────────────────────────────────┐
│                        Start the sample                              │
└─────────────────────────────────────────────────────────────┘
                              ↓
┌─────────────────────────────────────────────────────────────┐
│ When sample is ready to inject. Verify that the chromatographic system │
│    is ready and that injecting will not cause the new data window to │
│        overlap the previously injected sample data windows.          │
└─────────────────────────────────────────────────────────────┘
```

FIG. 6

Check that a chromatographic system method has progressed to the start "data window time" as specified by the current method
Move selector valve to deliver the fluid stream of the chromatographic system to delivery to the detector.
Signal the detector to begin data collection.
FIG. 7

MULTI COLUMN CHROMATOGRAPHY SYSTEM

CROSS REFERENCE TO RELATED APPLICATIONS

This application is divisional application of application Ser. No. 10/970,833, filed on Oct. 21, 2004, now U.S. Pat. No. 7,018,540 which is a divisional application of application Ser. No. 10/671,900 filed Sep. 26, 2003, now U.S. Pat. No. 6,808,635, which is a divisional of application Ser. No. 09/750,438 filed Dec. 28, 2000, now U.S. Pat. No. 6,635,173, all of which are incorporated herein by reference.

FIELD OF THE INVENTION

The present invention relates to a multi-column chromatography system, particularly suitable for high performance liquid chromatography (HPLC). The system optimizes a detector's data gathering ability, such as a mass spectrometer (MS), without sacrificing the quality or quantity of data collected. The system operates via the use of a staggered HPLC-MS operation sequence, through a plurality of individual chromatography systems as directed by a programmed computer protocol, and is suitable for both turbulent flow and laminar flow type systems.

BACKGROUND OF THE INVENTION

U.S. Pat. No. 5,919,368, owned by the assignee herein, provides an excellent review regarding the utility of separations by high performance liquid chromatography. As noted therein, the separation process relies on the fact that a number of component solute molecules in a flowing stream of a fluid percolated through a packed bed of particles, known as the stationary phase, can be efficiently separated from one another. The individual components are separated because each component has a different affinity for the stationary phase, leading to a different rate of migration for each component and a different exit time for each component emerging from the column. The separation efficiency is determined by the amount of spreading of the solute band as it traverses the bed or column.

The '368 patent ultimately goes on to describe an improved method of performing liquid chromatography comprising the steps of packing within a tubular container a substantially uniformly distributed multiplicity of rigid, solid, porous particles with chromatographically said particles, said particles having average diameters of not less than 30 μm and loading said surfaces with at least one solute that is reactive with said surfaces, by flowing a liquid mixture containing said solute through said column at a velocity sufficient to induce flow of said mixture within at least a substantial portion of said interstitial volume at a reduced velocity greater than about 5000. The aforementioned method: 1. dramatically enhances both the speed and capacity of both analytical and preparative chromatography for both small and large molecules such as biologicals and the like; 2. is operative with mobile phase velocities considerably greater than any previously employed with significantly improved results; 3. makes use of packed particle beds in which the particles are substantially larger than those previously used in the art; and 4. offers a process that is operative at pressures considerably below those taught by the prior art for turbulent flow chromatography. In that regard, attention is also directed to U.S. Pat. Nos. 5,772,874; 5,795,469; 5,968,367; 6,110,362 and 6,149,816, also owned by the assignee herein, which disclose other associated methods and apparatus for use in high performance chromatography applications.

With the above in mind attention is now directed to U.S. Pat. No. 6,066,848 which is said to provide a method and system for analyzing the composition of a plurality of fluid samples by chromatographic techniques. More specifically, the '848 patent states that the invention therein is able to distinguish between each of a plurality of fluid samples simultaneously electrosprayed from parallel liquid chromatography columns towards a miss spectrophotometer such that the mass spectra associated with each fluid sample can be reliable determined. That is, the '848 patent goes on to describe that a plurality of fluid samples are simultaneously separated by parallel liquid chromatography columns and are simultaneously electrosprayed towards an entrance orifice of a mass spectrophotometer. A blocking device having an aperture passing therethrough is positioned so as to block all but one of the fluid samples from passing into the entrance orifice of the mass spectrophotometer at any moment in time.

However, various problems have been identified with the above identified technique, which has in various forms been referred to as a "MUX" (i.e. multiplexed) liquid chromatography/mass spectrometry system. For example, such technology generally makes use of one pump to drive four sample streams. As a consequence, it is difficult to achieve optimum pressure in all streams, the back pressure may vary with column packing, the back pressure may vary with use, there can be poor reproducibility between streams, and there is a standing problem of "drift". Expanding upon this, there is no back-pressure monitoring, there is no way to link samples to a specific column, and when a single stream shuts down, e.g., in a four-column system, 25% of the data is lost along with 25% of the samples.

In addition, MUX technology, which makes use of a blocking disk, creates a potential for carryover as each spray impinging upon the disk may become cross contaminated. Furthermore, analyte date readout, by virtue of being multiplexed, leads to the feature that each of the electrosprays is analyzed over and over again in sequence. Accordingly, a varying mass spectrum reading will be generated for each of the plurality of fluid sample electrosprays over time. That being the case, MUX analyte data readout will appear as shown in FIGS. 1 and 2 herein, which makes clear that the number of data points is, in all cases, limited by the sampling rate of such a multiplexed system. More specifically, as shown in FIG. 1, data points are a function of sampling rate and are illustrated for sprays 1–4 v. elapsed time. FIG. 2 then illustrates that as a consequence of such multiplexing, the reported peak possibilities are prone to error, as different peaks may be drawn (dotted v. solid line) for the multiplexed data points so collected.

Stated another way, the MUX system can lead to insufficient peak data points for tracing along with a sacrifice in precision and sensitivity when operated at faster speeds. Furthermore, such problems are compounded in the case of multiple analytes.

Accordingly, there remains a need to develop a multi-colunm chromatography system that overcomes the disadvantages of the prior art and which provides a more reliable and accurate chromatographic separation along with maximum use of a detector's data gathering ability.

SUMMARY OF THE INVENTION

A method and apparatus for chromatographically analyzing each of a plurality of samples in a detector, including an autosampler which contains a plurality of samples for chromatographic analysis, a plurality of chromatography columns, a plurality of pumps associated with said plurality of columns to establish a flow of eluant from each of said plurality of columns and a detector for detecting compounds in said eluant from each of said columns. The apparatus further includes a valve positioned between said detector and said flow of eluant from said columns, said valve permitting each flow of eluant to reach the detector in sequence. A computer control device is included which automatically adjusts the introduction of samples from the autosampler into said plurality of columns as well as the position of said valve to sequentially deliver said eluant to said detector.

In an alternative embodiment, the present invention relates to an apparatus and method for chromatographically analyzing each of a plurality of samples in detector, comprising an autosampler to contain a plurality of samples for chromatographic analysis and a plurality of chromatographic systems, each system comprising one or more pumps and one or more each of said chromatography systems along with a valve positioned between said detector and said chromatography systems, said valve permitting each sample to reach the detector in sequence and a computer control device which adjusts the introduction of samples from said autosampler into said chromatography systems as well as the position of said valve to sequentially separate and deliver said compounds within said samples to said detector. Each chromatographic system is independent of the others, and each may consist of a number of components, including pumps, columns, valves, and heaters.

In a still further embodiment, the present invention relates to a chromatographic system containing a column, including a pump for eluting a mobile phase, and a detector for detecting compounds flowing out of said column, the improvement which comprises a computer control device that: (i) collects pressure readings over time from said pump to provide a tracing, (ii) compares such tracing to a stored pressure v. time tracing for said pump and (iii) elects to shutdown said pump when said tracing deviates from said stored tracing.

BRIEF DESCRIPTION OF THE DRAWINGS

FIG. 6 illustrates in block diagram format the functionality of the software system protocol of the present invention operating within the computer controller as applied in part to control of the autosampler.

FIG. 7 further illustrates in block diagram format the functionality of the software system protocol of the present invention operating within the computer controller as applied in part to initiate data collection at the detector.

DETAILED DESCRIPTION OF THE PREFERRED EMBODIMENTS

Figure 1:
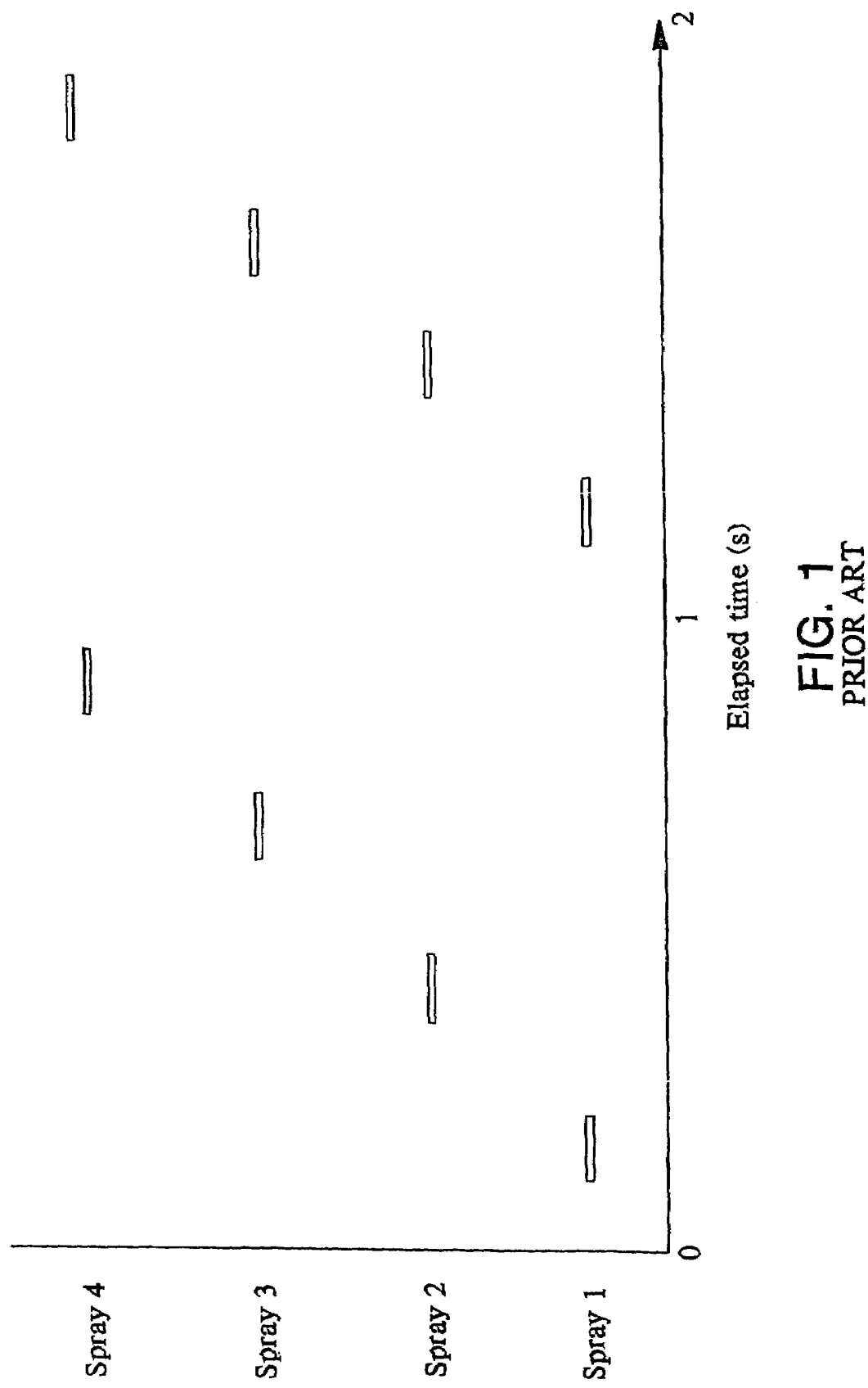
FIG. 1 illustrates the prior art analyte read-out for a multiplexed (MUX) HPLC system.
Figure 2:
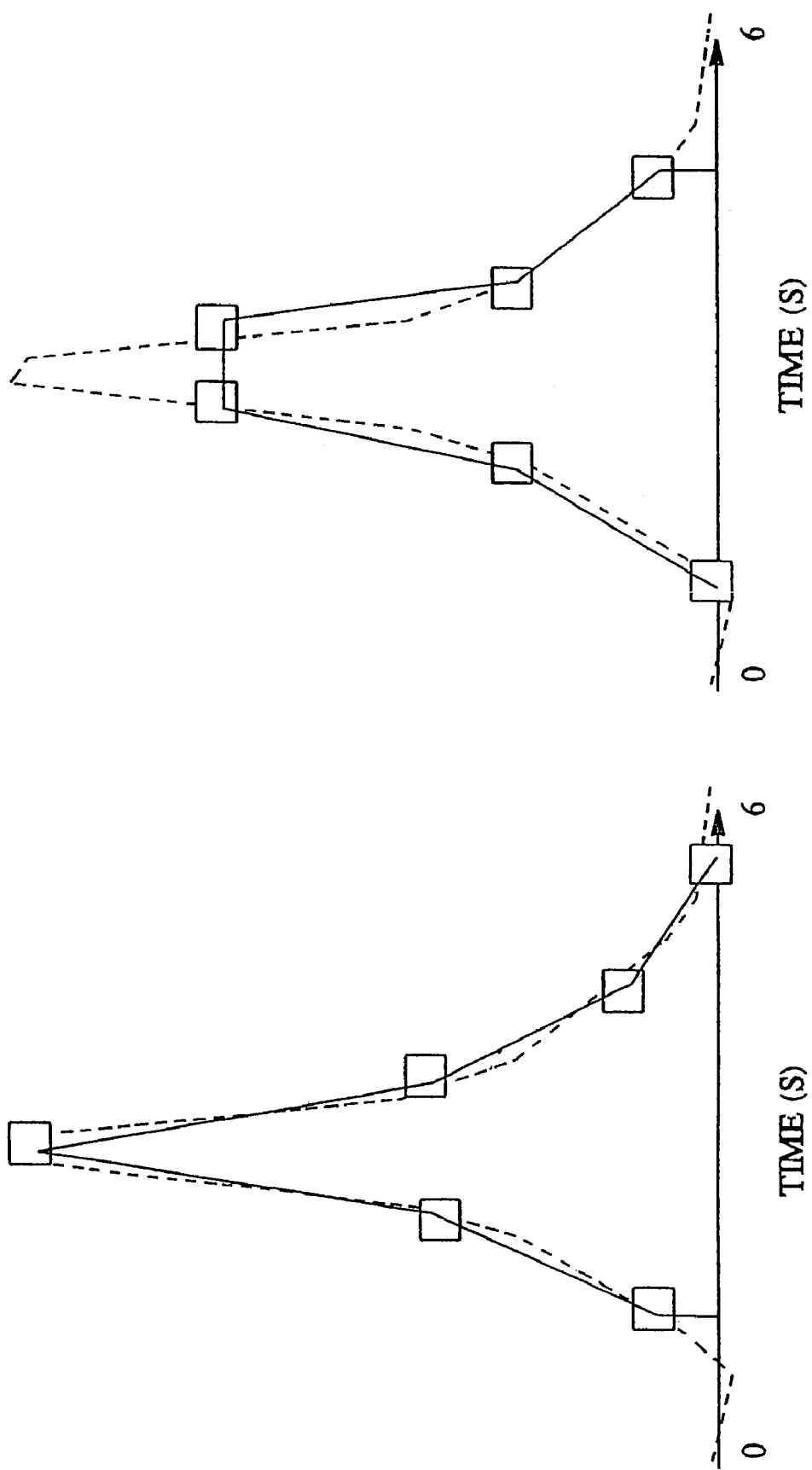
FIG. 2 illustrates the prior art peak measurement possibilities for a multiplexed (MUX) HPLC system.
Figure 3:
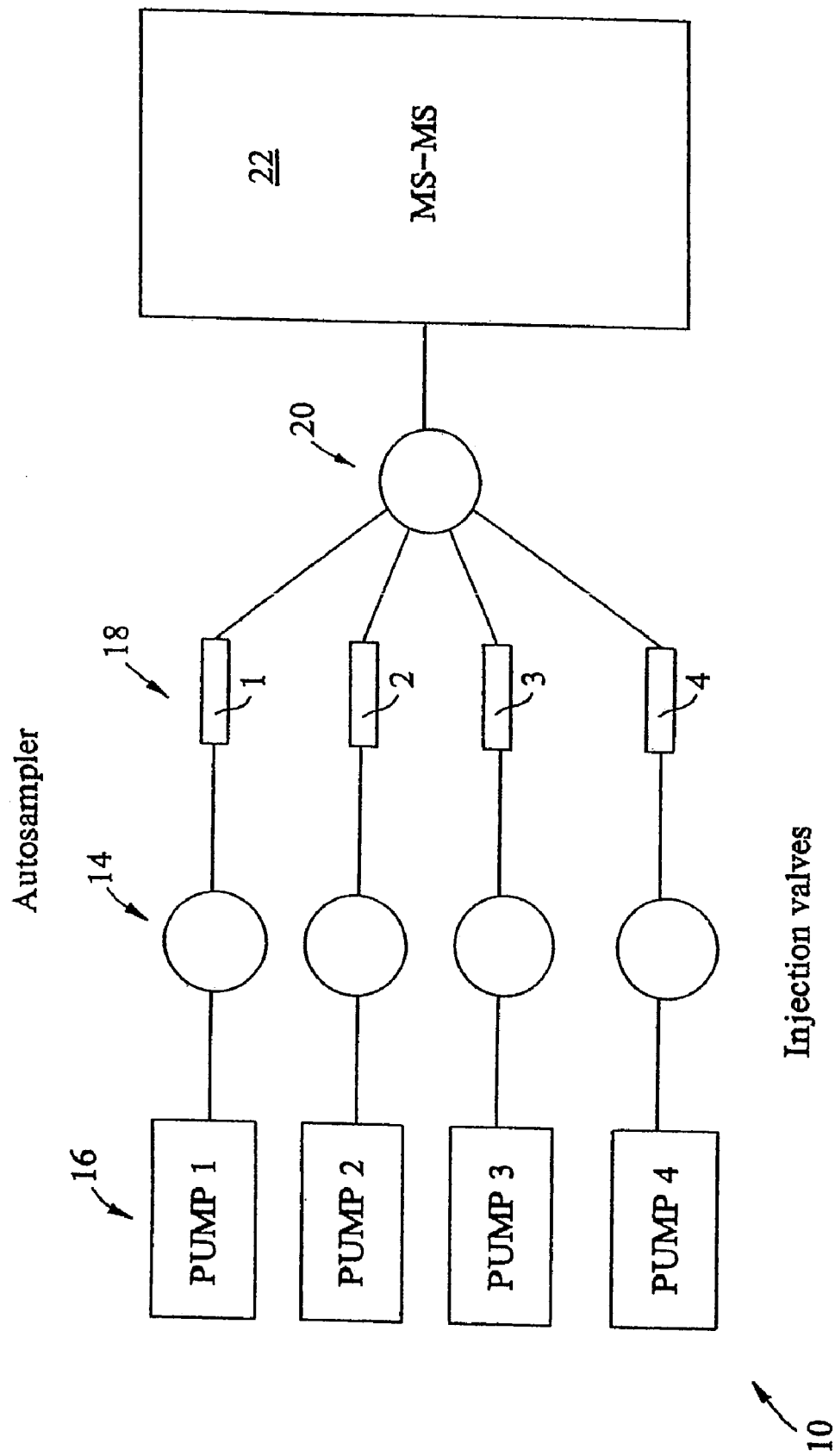
FIG. 3 illustrates in schematic view the multi-column chromatography system of the present invention.

One schematic view of the multi-column chromatography system 10 of the present invention is shown in FIG. 3. As can be seen therein, the system 10 contains an autosampler which includes a plurality of injection valves 14, a plurality of pumps 16, a plurality of columns 18, a selector valve 20 and a detector 22. Columns 18 may comprise a wide variety of columns useful for chromatographic analysis which can be used to direct a fluid sample into the entrance orifice of a given detector. For example, columns 18 may comprise high performance HPLC columns, capillary electrophoresis columns, gas chromatography columns, flow injection transfer lines, etc. In addition, although not shown, the system may also preferably includes a port valve, positioned before the columns, which in the case of a single column system (one or more pumps and one or more columns) operates to load sample in one direction, and elute in the opposite direction. In the case of a two column system, the port valve provides a similar function, and also provides a loop for eluting solvent.

However, as noted above, the present invention may also be described as an apparatus and method for chromatographically analyzing each of a plurality of samples in a detector, comprising an autosampler (with preferably two sampling arms) which contains a plurality of samples for chromatographic analysis, along with a plurality of chromatographic systems, each system comprising one or more pumps and one or more chromatography columns. In that regard, it can be appreciated that each chromatographic system is controlled by the computer controller herein to ensure that samples are introduced by the autosampler to avoid overlap at the detector end, and to ensure maximum use of the detector's time as a detector. In that regard, the invention herein preferably relates to the use of, e.g., four (4) independent chromatography systems, wherein each system contains one (1) or more pumps and one (1) or more columns. Alternatively, in a more preferred embodiment, the invention herein relates to the use of four (4) independent chromatography systems, wherein each system contains two (2) pumps and one (1) column, such that one pump is devoted to loading the column with sample, and one pump for elution. As such, the invention herein preferably relates to the use of either of such previously mentioned options, to the extent that at least two (2) of the chromatography systems so defined are incorporated into the sequencing chromatography apparatus of the present invention.

Figure 4:
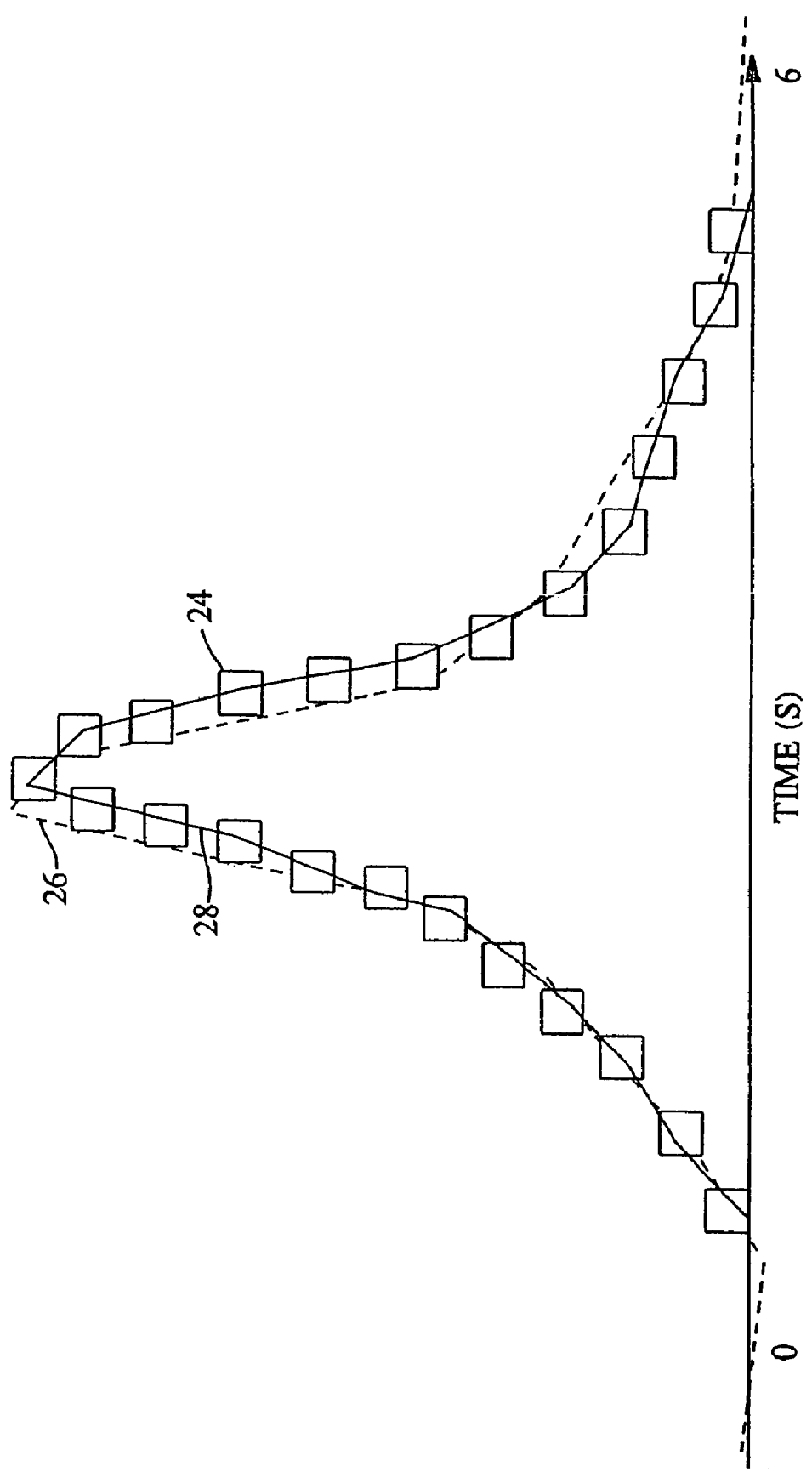
FIG. 4 illustrates sampling points and peak profile as a result of the multi-column chromatographic system of the present invention.

As can next be seen in FIG. 4, according to the present invention, the number of data points 24 available in the present invention is consistent with the number of data points available from a standard single-column/single detector configuration. That is, the number and quality of data points 24 from a column chromatography procedure are undisturbed in the present invention, since the present invention relates to the unique sequential operation of a plurality of chromatography systems such that a given point in time such that quality and quantity of data is not sacrificed. As can be seen in FIG. 4, according to the present invention, curve 28 is generated, which represents a more precise curve fitting than that which may be obtained by the multiplexed system of the prior art, which inherently contains fewer data points as well as-the possibility to report less precise curve 26. In that regard, it is worth noting that no matter how fast a multiplexed system is sampling, the invention herein will, e.g., in case of a four (4) samples to be analyzed, report four times more information (data points) for any given peak.

Figure 5:
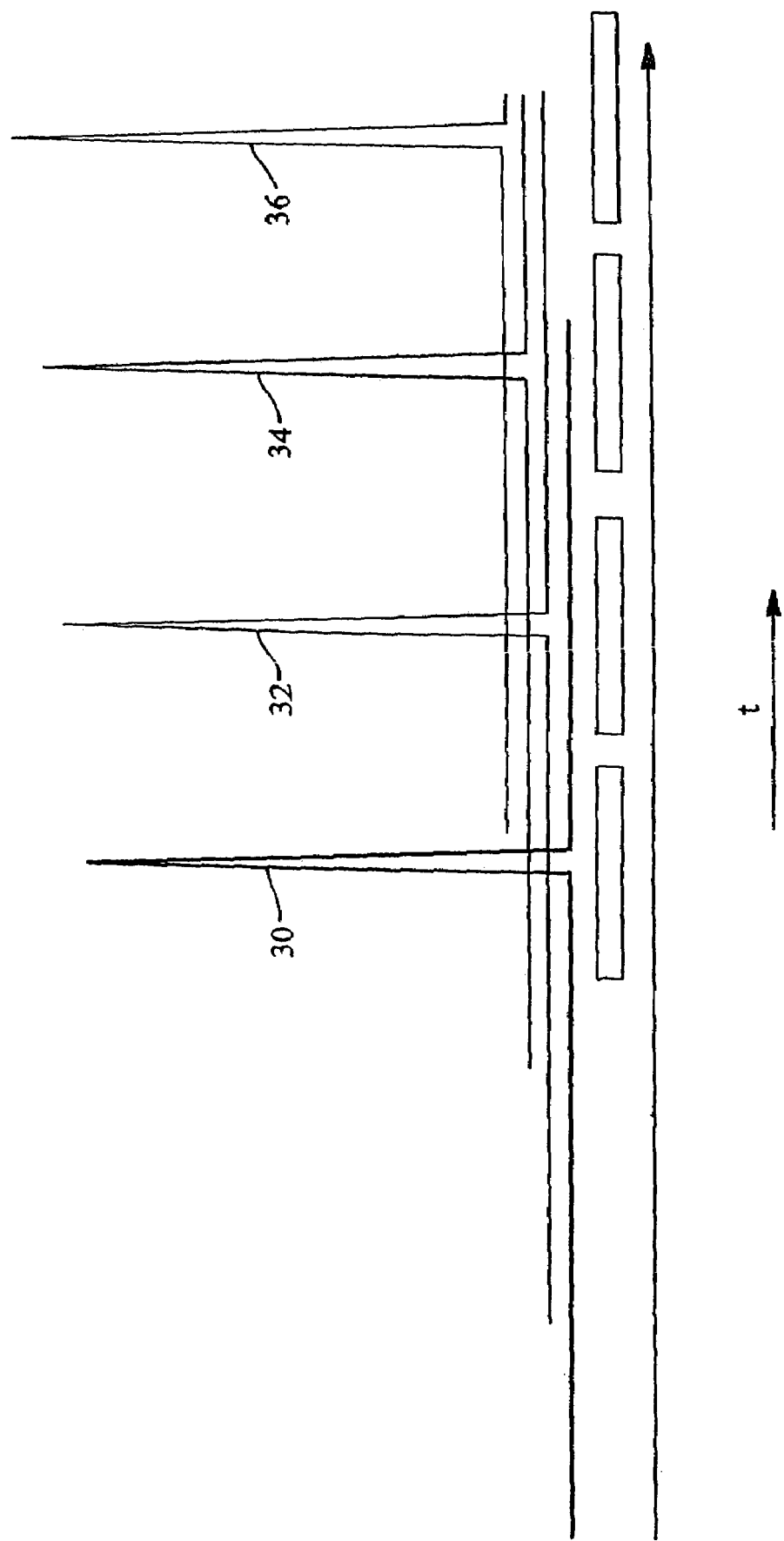
FIG. 5 illustrates the typical results of the multi-column chromatography system of the present invention.

Expanding upon the above, attention is directed next to FIG. 5, which illustrates curves 30, 32, 34, and 36, as obtained herein, due to procedural benefit of controlled staggered/sequenced injections. As can be seen, the detector analyzes each curve in sequence. In such regard the detector herein functions to detect and report curve 30, while those samples responsible for curves 32, 34, and 36, although in the process of being eluted in the column, have not yet exited from the column. Such programmed chromatography sequencing is provided herein by a computer control device which, upon consideration of when the target sample is likely to exit the column, adjusts the introduction of samples from the autosampler into the columns to sequentially deliver eluant containing sample for sequenced detection. In other words, the computer controller herein considers the samples in the autosampler, and the input of information concerning their anticipated data-collecting window at the detector, and selects those samples from the autosampler for introduction into the system to maximize detector use.

The computer control device of the present invention therefore adjusts the introduction of sample from the autosampler, as well as the position of valve 20 (FIG. 3) to sequentially deliver eluant to the detector. However, the computer control device herein preferably functions to provide other important blocks of information to the user. This is more specifically illustrated in FIG. 6, which provides a schematic overview of the functionality of the software system protocol within the computer control device of the present invention as applied to the autosampler. As shown therein, the control device first checks that the autosampler/probe is ready to start a sample and that sufficient time has passed since the last sample start. The controller then checks that a chromatographic system as herein defined is ready to accept a sample. This is determined by the time remaining for the currently running elution protocol, and this prediction therein optimizes the overall system efficiency. By contrast, waiting for the chromatography system to indicate that it is "ready" before starting the sample would elongate the cycle time by that amount of time between starting the sample and the sample being "ready" to inject.

The controller then determines which sample corresponds with the "ready" chromatography system. When sample information is entered, the user has the option of specifying a particular chromatography system or allowing any of the available systems to be used for the sample. The sample is then started and when the sample is ready to inject, the controller will verify that the chromatography system is ready and that injection will not cause the new data window (i.e., the ensuing report of the chromatographic peaks) to overlap the previously injected sample data windows.

FIG. 7 illustrates the detector and selector valve control of the present invention. As shown therein, the controller checks that a chromatographic system elution protocol ("method") has progressed to the start "data window time" as specified by the current method. The selector valve is then moved to deliver the fluid stream of the chromatographic system to deliver sample to the detector and the detector is signaled to begin data collection.

Figure 8:
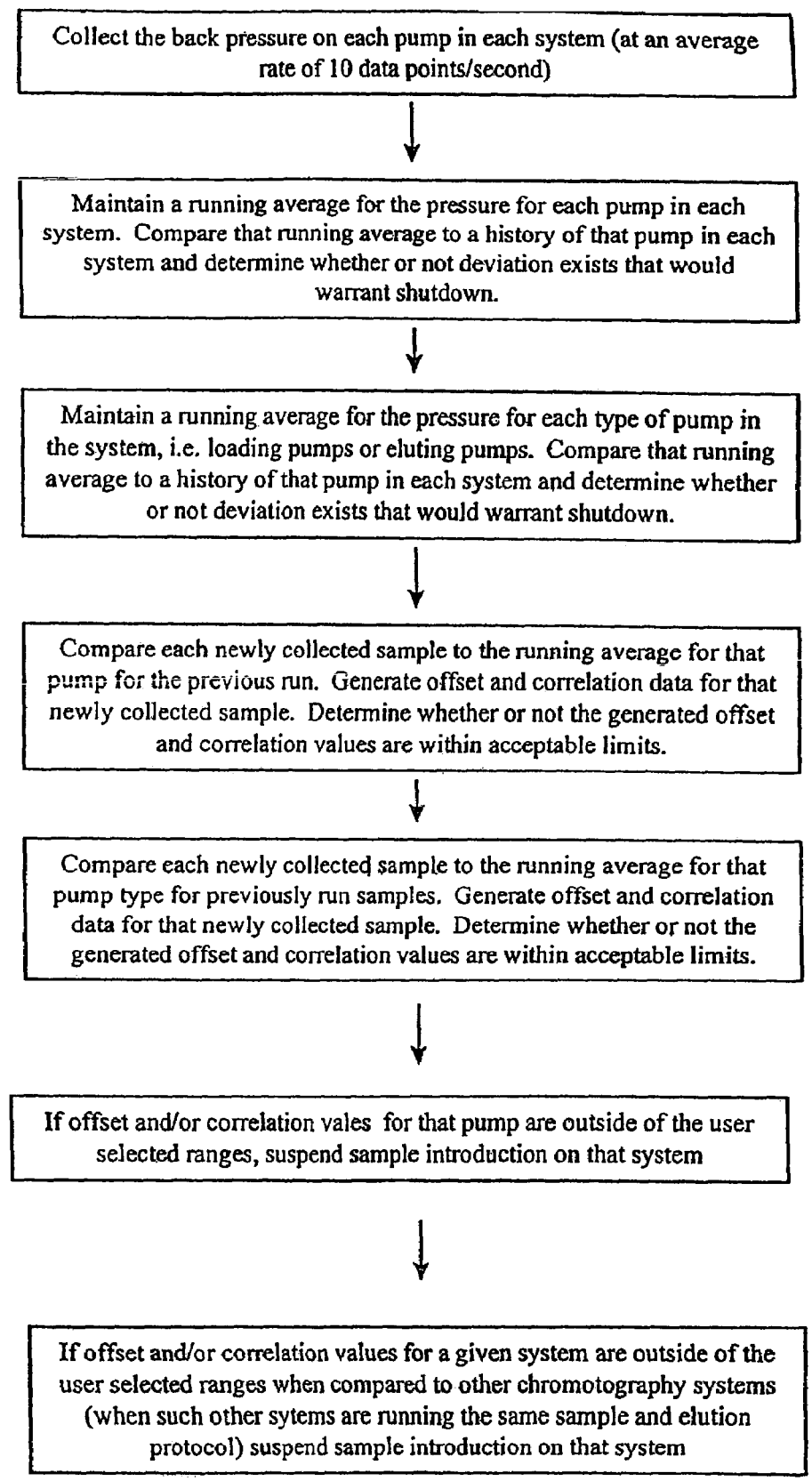
FIG. 8 illustrates in block diagram format the functionality of the software system protocol of the present invention as applied to the monitoring of system pressure.

FIG. 8 illustrates the pressure control of the invention herein as provided by the computer controller. More specifically, the controller will collect back pressure readings for each pump 14 in each chromatography system at an average rate of 10 data points per second. As noted above, the chromatography system herein refers to one or more pumps and one or more chromatography columns within the disclosed chromatography apparatus.

The computer controller therefore maintains a running average for the pressure for each pump in each system. The controller then compares that running average to a history for that pump in each system and determines whether or not deviation exists that would warrant a shutdown. In a related manner, the controller maintains a running average for the pressure for each type of pump in the system, i.e., loading pumps or eluting pumps. The controller again compares that running average to a history for that pump in each system and again determines whether or not deviation exists that would warrant a shut-down.

The controller herein also compares each newly collected sample to the average of pressure for that pump for the previous run. The controller then generates offset and correlation data for that newly collected sample. In other words, the controller identifies whether or not the data points vary in intensity and location (i.e., that point in time) from the average pressure v. time tracing generated from one or more previous runs. The controller then determines whether or not the generated offset and correlation values or tracings are within acceptable limits. In a preferred embodiment, when the generated pressure v. time tracing deviates from the stored tracing by, e.g. the slope or shape of the tracing between at least two pressure readings, the system may be shutdown.

In addition, and in related context, the controller also compares each new collection of sample back-pressure data points for a given pump to the running average based upon pump type. Once again, the controller generates offset and correlation data, and determines whether or not the generated offset and correlation values are within acceptable limits. If offset and correlation values for the pump are outside of a user selected range, sample introduction into the system is suspended.

Finally, if offset and correlation values for a given system are outside of user selected ranges when compared to other chromatography systems (when such other systems are running the same sample and elution protocol) sample introduction on the system will also be automatically suspended.

One particularly preferred column herein, but by no means limiting, are those columns which include a substantially uniformly distributed multiplicity of rigid, solid, porous particles with chromatographically active surfaces, said particles having average diameters of greater than about 30 µm, the interstitial volume between said particles being not less than about 45% of the total volume of said column; and means for loading said surfaces with at least one solute that is reactive with said surfaces, by flowing a liquid mixture containing said solute through said body at a velocity sufficient to induce flow of said mixture within at least a substantial portion of said interstitial volume at a reduced velocity greater than about 5,000.

To these ends the present invention is directed to the use of a chromatography column or body in the sequenced chromatography system herein that is formed as a substantially uniformly distributed multiplicity of rigid, solid, porous particles having substantially uniform mean cross-section dimensions or diameters of not less than about 30 µm, typically 50 µm or greater up to, but not limited to, 1000 µm in certain instances as will be delineated hereinafter. The term "particle" as used herein should not be construed as limited to any particular form or shape, regardless of symmetry or lack thereof, aspect ratio, regularity and the like.

The term "solid" as used herein, is intended to refer to the physical state of the matter and should not be construed to exclude porous particles. The particles are selected from a range of various sizes and shapes and are held together in a body or column as by pressure, sintering and the like so that interstitial channels having a total interstitial volume of not less than about 45% of the total volume of the column are formed between the particles. The surfaces of the particles, including the inner surfaces of the pores in the particles, may be chromatographically active, as by being coated with chromatographic stationary phase layers. This method includes the step of flowing through the column a fluid mixture containing at least one solute or suspended phase that is interactive with the particles' surfaces in order to load the column. Because of the nature of the particles and packing in the column, the flow of the fluid mixture through the column can be at a high flow rate, preferably at an average reduced velocity (i.e., $ud[p]/D$ wherein "u" is the mobile phase velocity, "d[p]" is the packing particle diameter and "D" is the diffusion coefficient in the mobile phase) greater than about 5000, and including, in certain instances to be described hereinafter, reduced velocities values as high as 70,000 or higher. It is believed that under such conditions, turbulent flow of the mixture is induced within at least a major portion of the interstitial volume, and it is postulated that such turbulent flow in fact enhances the rate of mass transfer, thus increasing the dynamic capacity of the column.

The particles described above are preferably formed from materials that are incompressible, which term is to be understood to mean that the time rate of changes of the densities and volumes of the particles under pressures of at least about $5 \times 10^3$ psi, (including outlet column frit retainer) remains substantially zero, and the particles therefore will substantially resist plastic deformation even at such high pressure. The particles are shaped and selected in a range of sizes and shapes such that they can be packed at a pressure sufficient to form a column characterized in having interstitial channels formed between the particles. Because of the irregularity of the particles, it will be recognized that the interior walls of such channels are necessarily quite rough in configuration. While it is believed that at least the majority of channels have mean cross-section diameters substantially not less than about 4 µm, the interstitial volume fraction (i.e. the total volume of interstitial channels between the particles) should not be less than about 45% of the total volume of column. It will be appreciated that typical columns have interstitial volume fractions less than about 45%, more particularly ranging from about 35% to 42%. The surfaces of particles are chromatographically active either per se as is well known in the art, or by treatment, as by coating, with any of the many known chromatographically active, stationary phase layers, also as well known in the art.

As noted, in order to insure the formation of the desired uniform density column with the preferred interstitial fraction and preclude collapse under operating pressure, the particles used to pack a column for use in the present invention of sequenced chromatography analysis may include rigid solids that must necessarily be incompressible at packing pressure of at least about $5 \times 10^3$ psi, preferably up to pressures as high as about $1 \times 10^4$ psi. To that end, the preferred particles are formed from materials such as alumina, titania, silica, zirconia, vanadia, carbon, various relatively inert metals, and combinations thereof.

In that regard, the chromatography column used herein may include columns used under conventional laminar flow regimes. The columns may therefore be constructed of particles, which due to a lack of requisite rigidity are run at low flow rates and pressure drops. Such particles may have average particle sizes less than about 30 microns and as small as about 1 micron. It is understood that under these operating conditions, the analysis times are relatively long and the reduced velocities may be as small as 1.

In addition, the invention herein may include the use of a substantially uniform elongated chromatography column containing chromatographically reactive surfaces, means for injecting into said column a discrete volume of liquid mixture containing at least one solute that is reactive with said surfaces so as to load said column, and means for flowing eluant fluid through said loaded column, wherein the means for flowing said eluant fluid comprises means for injecting at least one discrete plug of said eluant fluid into said column adjacent the input of said column so as to maintain minimized spatial step separation between said plug and said discrete volume of liquid mixture as said plug and volume traverse the column wherein said column and said means for flowing are configured such that the flow of said volume of eluant traverses said column at a reduced velocity greater than about 5000.

The invention herein is also applicable to chromatography columns having chromatographically reactive surfaces, including the steps of flowing through said column a discrete volume of a liquid mixture containing at least one solute that is reactive with said surfaces, and eluting from said surfaces said solute bound thereto, by flowing eluant fluid through said column, comprising the steps of injecting at least one discrete volume of an eluant fluid into the flowstream in said column such as to maintain minimized spatial separation between said discrete volumes as the latter traverse said column at a reduced velocity great than about 5,000.

The invention herein is also applicable to separating relatively low molecular weight compounds from compounds having relatively high molecular weights substantially an order of magnitude greater or more than said low molecular weight compounds in a liquid mixture of said compounds, comprising a chromatographic body formed of substantially uniformly distributed multiplicity of rigid, solid, porous particles with average diameters of not less than about 30 µm, and average pore diameters sufficiently small to substantially exclude introduction of said compounds of relatively high molecular weight into said pores, the surfaces of said particles and pored being hydrophobic and chromatographically active, and a means for flowing said mixture at a velocity sufficient that the flow of said mixture within at least a substantial portion of the interstitial volume between said particles is at a reduced velocity greater than about 5,000 until said high molecular weight compounds have exited said body, and a means for eluting said relatively low molecular weight compounds from said body with an eluant liquid at a reduced velocity less than about 5,000, after said high molecular weight compounds have exited from said body.

With consideration now shifted to the detector 22, such is preferably any type of detector that is employed in chromatography systems to detect the samples eluted through the columns. Those skilled in the art will therefore recognize that detector 22 may comprise an ultraviolet detector, or more preferably, a mass spectrophotometer. The detector therefore provides identification of the desired component compounds of a sample by determining exactly when such a desired component compound is eluted from the exit end of the column.

The invention herein is suitable for any type of chromatography type configuration making use of a multiple column configuration. In that regard, the invention herein is applicable to analytical chromatography as well as preparative chromatography systems. In that regard, the invention is applicable herein to conventional HPLC systems relying upon a mass spectrometer detector which system undergoes conventional programmed liquid flow velocities and makes use of conventional type gradient systems. However, while such use of conventional chromatography systems is suitable herein, the invention herein advances the efficiency of such known systems by uniquely linking up a plurality of such systems to a single detector to optimize the detectors data gathering ability without sacrificing the quality or quantity of data collected.

What is claimed is:

1. A chromatography system comprising:
   a chromatography column capable of separating compounds in a mobile phase;
   a pump for eluting said mobile phase through said chromatography column;
   a detector for detecting said separated compounds flowing out of said chromatography column; and
   a computer control device for collecting pressure readings over time from said pump and providing a pressure versus time tracing based on said collected pressure readings, said computer control device comparing said pressure versus time tracing to a stored pressure versus time tracing and shutting said pump down when said pressure versus time tracing deviates from said stored tracing by more than a predetermined limit.

2. The chromatographic system of claim 1, wherein said pressure versus time tracing deviates from said stored tracing by the slope or shape of the tracing between at least two pressure readings.

3. The chromatographic system of claim 1, wherein said stored tracing comprises a tracing of previously collected pressure versus time data for said pump.

4. The chromatographic system of claim 1, wherein said stored tracing comprises a tracing of pressure versus time data for a predetermined pump type.

5. The apparatus of claim 1, wherein said chromatography column comprises a substantially uniformly distributed multiplicity of rigid, solid, porous particles with chromatographically active surfaces, said particles having average diameters of greater than about 30 μm, the interstitial volume between said particles being not less than about 45% of the total volume of said column; and means for loading said surfaces with at least one solute that is reactive with said surfaces, by flowing a liquid mixture containing said solute through said body at a velocity sufficient to induce flow of said mixture within at least a substantial portion of said interstitial volume at a reduced velocity greater than about 5,000.

* * * * *